United States Patent [19]

Fakhrai

[11] Patent Number: 4,622,955
[45] Date of Patent: Nov. 18, 1986

[54] SURGICAL RETRACTOR FOR DISSECTION OF INTERNAL MAMMARY ARTERY

[76] Inventor: Mehdi Fakhrai, 1242 Barrington Ave. #201, Los Angeles, Calif. 90025

[21] Appl. No.: 772,997

[22] Filed: Sep. 5, 1985

[51] Int. Cl.[4] .............................................. A61B 17/02
[52] U.S. Cl. ...................................................... 128/20
[58] Field of Search ............................................ 128/20

[56] References Cited

U.S. PATENT DOCUMENTS

| | | | |
|---|---|---|---|
| 2,642,862 | 6/1953 | Jackson | 128/20 |
| 3,572,326 | 3/1971 | Jensen | 128/20 |
| 3,643,655 | 2/1972 | Peronti | 128/20 |
| 4,099,521 | 7/1978 | Nestor et al. | 128/20 |
| 4,122,844 | 10/1978 | Rabban | 128/20 |
| 4,143,652 | 3/1979 | Meier et al. | 128/20 |
| 4,254,763 | 3/1981 | McCready | 128/20 |

Primary Examiner—William H. Grieb
Attorney, Agent, or Firm—Mehdi Fakhrai

[57] ABSTRACT

A surgical retractor is to be mainly used for dissection of the internal mammary artery. It is fixed to the side of the operating bed by a clamp which can be moved over the rail for the desired place. It's pole will be at either side that internal mammary artery is intended to be dissected, side arm of the pole will be over the patient and holding the crank mechanism, by placing the hooks of the retractor at the edge of the sternum after being split at the middle, and cranking the handle. The crank portion of the retractor, which is adjustable over the side arm of the pole, will pull and elevate the side of the chest and hold it in position for the time that is needed for the dissection of the internal mammary artery. Adjustment can be done with the crank part for better vision. After completion, release of the lever would allow the crank mechanism to be turned in the opposite direction, counter clockwise, the cord to become loose and the hooks to be free. The retractor can be removed by releasing it from the side of the bed by the loosening of the holding clamp. This retractor can be used for any other procedures that require elevation and retraction of part of the chest.

A different type of pole (rod-shaped) and a different attachment for the crank mechanism can be used that would be adjusted easier by one screw.

1 Claim, 5 Drawing Figures

SURGICAL RETRACTOR FOR DISSECTION OF INTERNAL MAMMARY ARTERY

BACKGROUND OF INVENTION

This surgical instrument is made for holding and elevation of part of chest & making possible to have good vision for dissection of Internal Mammmary Artery in Cardiac Surgery. There have been several other retractors in the market that one of them is being used widely (Favarolo Retractor) that is comprised of two poles for holding at side of operating table and a bar across the poles and two adjustable arms by clamps and screws with hooks at the end of them. They can be moved over the bar and are fixed individually to the edge of split sternum. In practice needs force to elevate side of chest and each of them is positioned and tightened individually by help of another person.

The other retractors that are mentioned in references are not widely used and are not very practical for dissection of the internal mammary artery and they speak by themselves that are not being used.

Present retractor has only one pole and it can be applied by one person and crank mechanism will elevate and pull outward side of chest to proper level and does not need force of person for elevation. As two hooks are applied at the same time, chance of fracture of sternum is minimal or nil, also it can be adjusted at small increment as needed.

SUMMARY OF INVENTION

This retractor is mainly for dissection of internal mammary artery and it provides good view of area that needs to be seen for dissection of internal mammary artery. It has one pole that is being fixed to the side of bed by clamp—the side that internal mammary artery intended to be dissected. (The clamp is being fit at a rail that is universal at any hospital operating table). It can be moved up or down at the side of the bed on rail for proper level of retractor. By placing two hooks that are adjustable and can be close together or apart to accomplish good position for different size of thorax and sternum. They are hooked after sternum is split at the middle to the edge of sternum and hold thickness of bone. The crank mechanism that is at the horizonital arm of the pole over the side of the chest will elevate and also pull outward the anterior wall of the thorax, and will hold it position at the proper level for good vision to dissect the internal mammary artery. It can be adjusted easily by cranking the handle. After finishing dissection it can be released by pulling the lever and cranking opposite direction. The crank part is also movable and adjustable over the horizontal arm of the pole, and will be fixed by two screws.

BRIEF DESCRIPTION OF THE DRAWING

FIG. (1): Side perspective view showing pole that will be fixed to the side of operating table, horizontal arm that crank mechanism is being attached and cord and hooks.

FIG. (2): Front view of crank mechanism and its attachment to the horizontal part of the pole and its connection to the cord.

Figure 1:
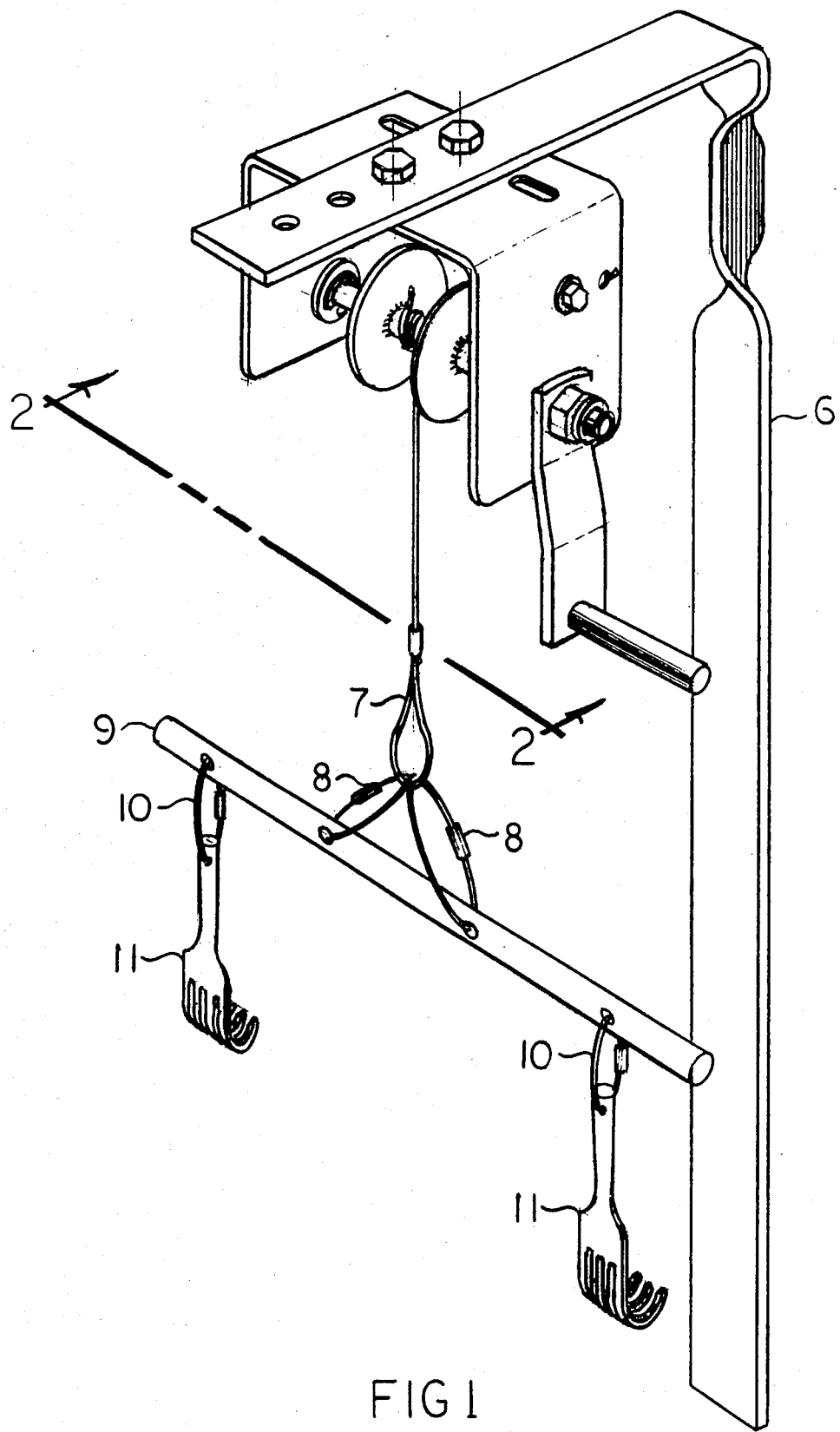
Figure 2:
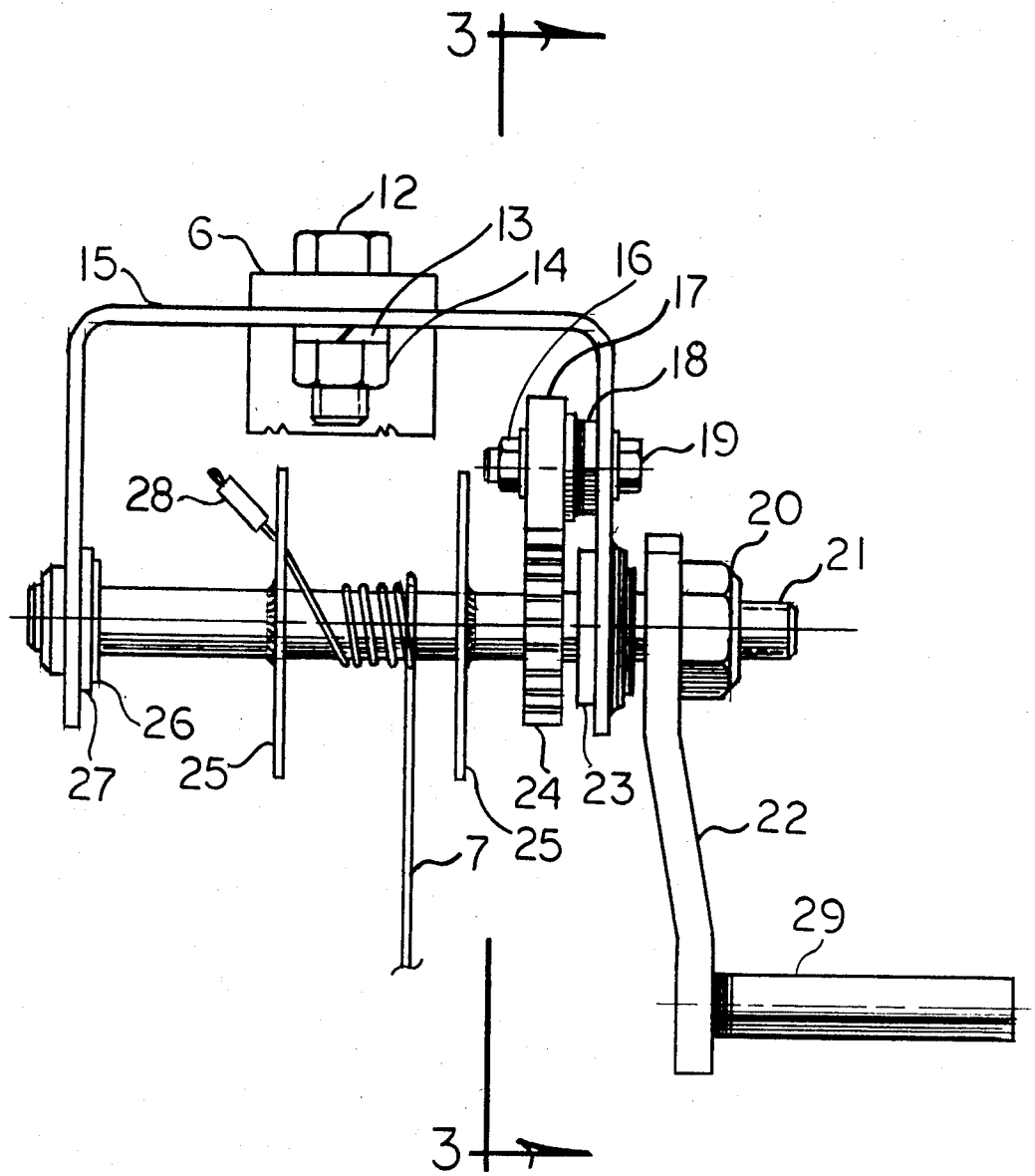
Figure 3:
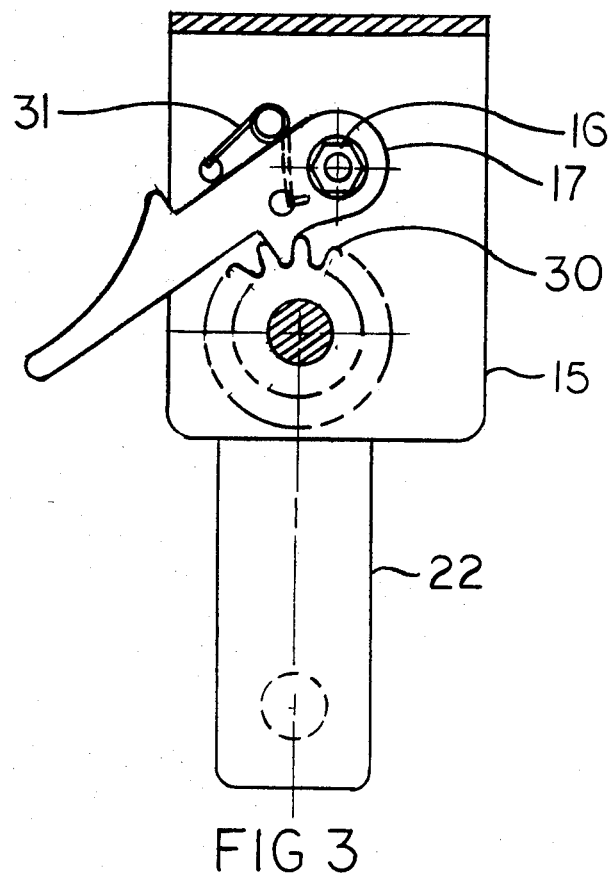

FIG. (3): Sectional view of the crank mechanism and handle at line 3.

FIG. (4): Side perspective view showing different type of pole.

FIG. (5): Front view of crank mechanism with different type of attachment.

The retractor is made of three parts: pole and horizontal arm, crank mechanism, cord and hooks.

DESCRIPTION

Referring in detail to the drawings, this surgical apparatus is comprised of a flat stainless steel pole with a twist at its vertical part for strength and horizontal arm. (6)

The lower part of the pole is attached to the side of the operating table by a clamp that can be moved over a rail (universal on any hospital bed). It can be adjusted up or down (toward head or foot). Also, the length of the pole can be adjusted by how far it is pushed below the rail at the bedside (at proper level for width of the thorax of the patient). It is attached to the side that the internal mammary artery is intended to be dissected (right or left).

The crank mechanism is attached by two screws (12), (13), (14) to horizontal arm of the pole, and it can be adjusted inward or outward and fixed by tightening screws in the proper holes for the desired position.

This retractor is placed at the side of the operating table after the surgery is underway and the sternum is split at the middle. Hooks (11) will be placed under the sternal bone and it can be adjusted up or down, close or far from each other for proper adjustment due to the different size of thorax of the patient. Hooks are attached to the horizontal, stainless steel rod (9) near each end by a metallic cord (10), and this can be shortened if needed by making a twist in it. The rod is attached by two metallic cords (8) near the mid portion to the main cord (7). The proximal part of the cord (7) is attached to the wheel of the crank mechanism (28). The crank mechanism has a case (15) that attaches it to the horizontal arm of the pole (6) and is fixed to it by screws (12), (13), (14).

The crank mechanism has a spring (31), lever (17), and screw to hold it in place at the side of case (16), (18), (19). The lever has a tongue that is over a gear (24). The gear and wheels (25) are over a rod (21) at the crank mechanism and is held in place by washers and screws (23), (26), (27), (20). Turning this rod by the handle on the arm (22) the holder (29), will turn the gear (24) one way (clockwise) when the lever is in place over the gear. By elevating the lever, the tongue of the lever will come out from the gear teeth (30) and will be free to turn freely. A spring will hold the lever and tongue over the gear, between the teeth (30), at all times when in position.

By turning the rod (21) and wheels (25) in the crank mechanism, it will wrap the metalic cord (7) around the rod (21), between the wheels (25), and will shorten the cord (7), and will pull the rod (9), and hooks (11). This will elevate and pull outward the anterior part of the chest and will give the desired view under it for dissection of the internal mammary artery, and will hold it in the desired position until the work is done.

For removing the retractor, first the lever will be elevated at the crank mechanism (17) to free the tongue of the lever from the grear (24) then by turning the handle and arm (22), (29) counter clockwise, it will loosen the cord (7) and hooks (11). The anterior part of the chest will go down, and the hooks (11) can be removed from the edge of the sternum. Then the retractor can be removed by loosening the holding clamp that is holding the pole of the retractor (6) at the side of the operating table.

Figure 4:
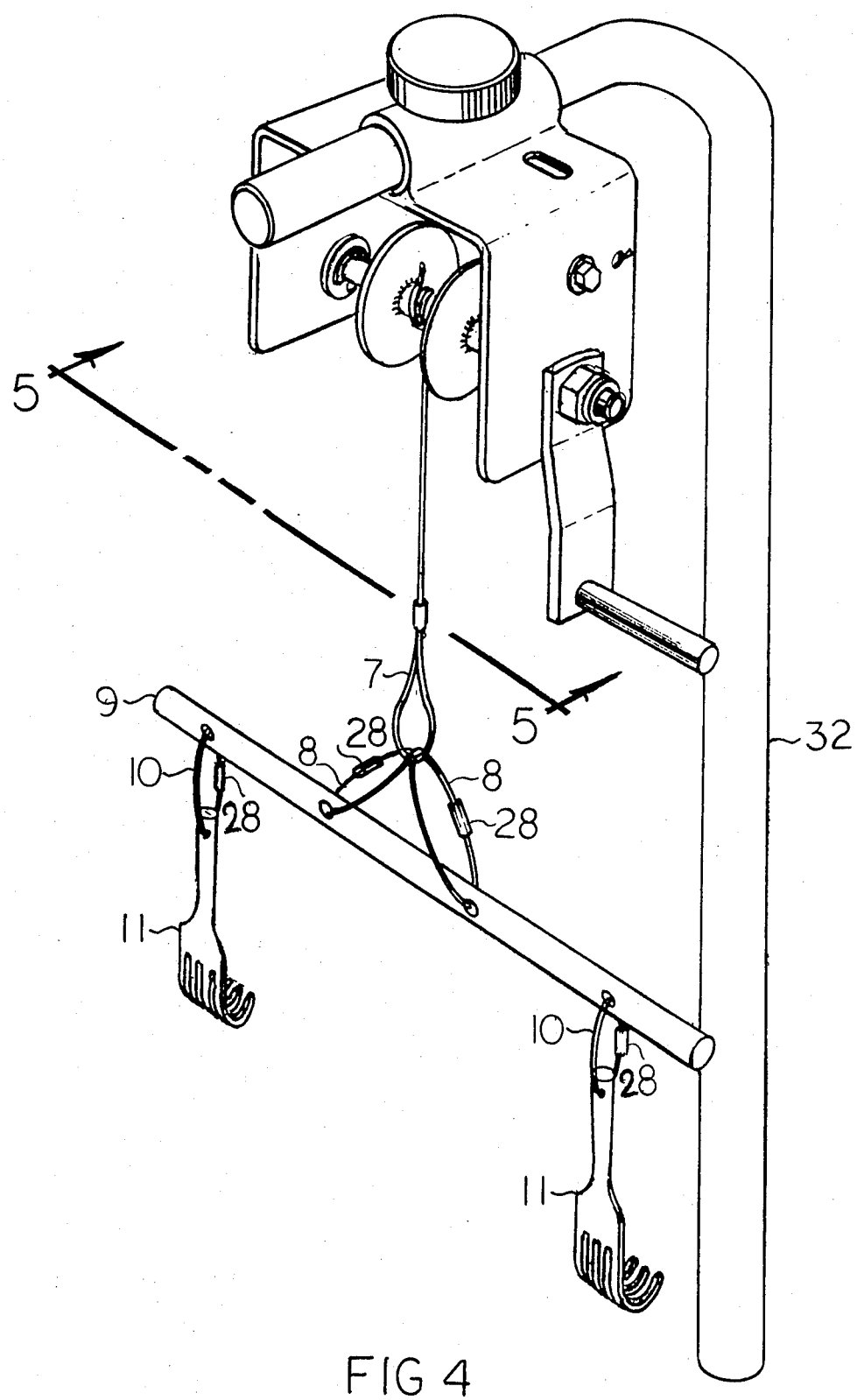
Figure 5:
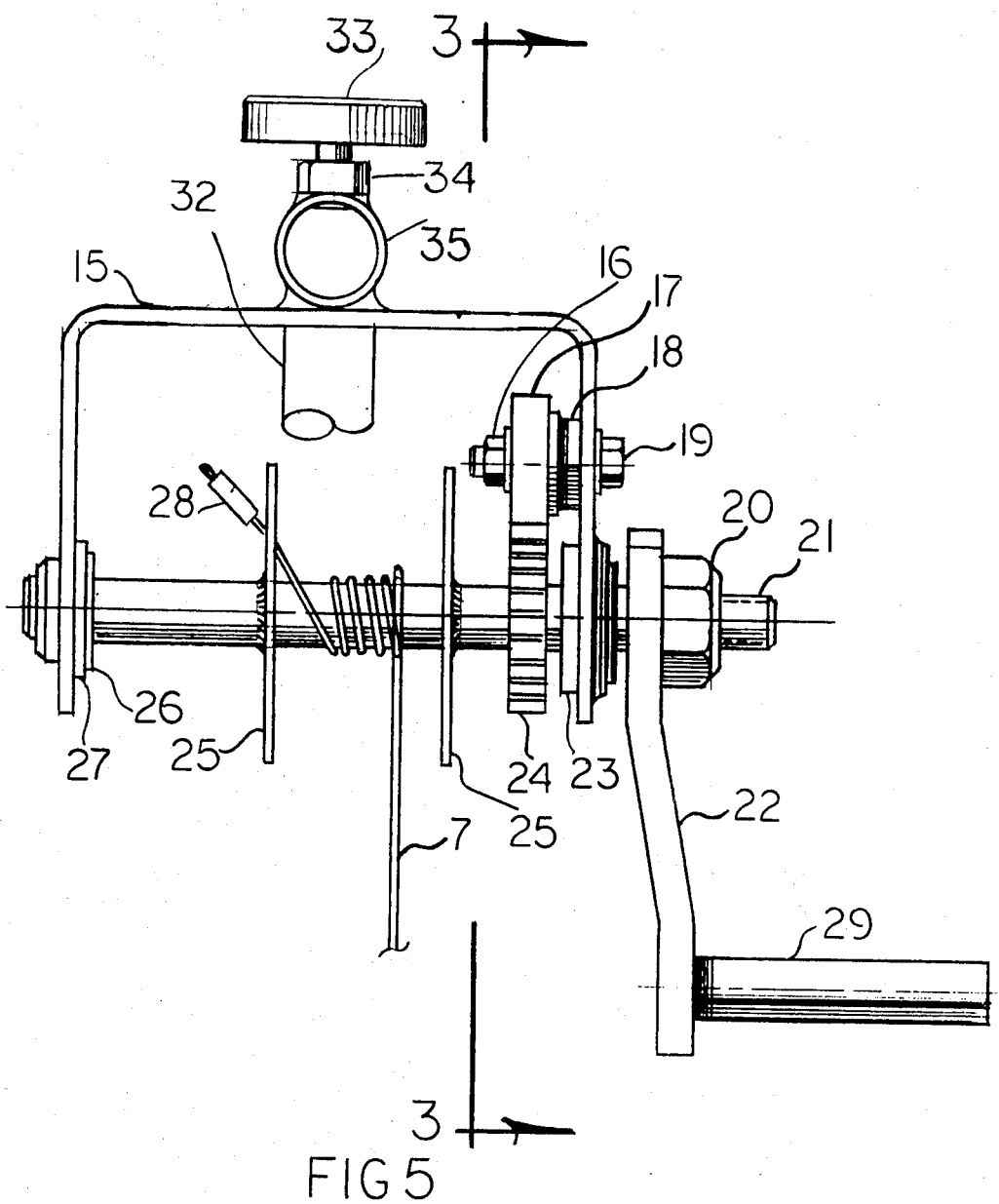

In FIGS. 4 and 5, a different type of pole which is round (32) is being shown and the crank mechanism attachment (35) to the side arm of the pole is held by the screw (33), (34). Their work is identical to what has been described and adjustment over the side arm may be easier. All parts of this retractor are made of stainless steel that will not rust by autoclaving.

I claim:

1. A surgical retractor device particularly adapted for use in thoracic procedures where it is desired to urge the sternum both laterally outwardly and vertically upwardly such as for mammary artery dissection, said device comprising a vertically extending member having a lower end secured relative to the patient support laterally outwardly of such patient and an upper end vertically above the position of the sternum of such patient, an elongate rigid member extending generally parallel to the sternum, a pair of spaced apart hooks having one end flexibly secured to said rigid member at spaced apart points and having a hook means on the distal and adapted for attachment over the split sternum, flexible retraction means having one end secured to said rigid member between said points and the other end operably secured to said vertically extending member, and means for retracting said flexible means away from said sternum by crank mechanism that is secured to said elongate rigid member and operates by turning handle to crank and hold at desired position toward said vertically extending member whereby said split sternum section is urged both vertically upwardly and laterally outwardly by both of said spaced apart hooks carried by said rigid member.

* * * * *